US011763655B2

(12) United States Patent
Negre et al.

(10) Patent No.: US 11,763,655 B2
(45) Date of Patent: *Sep. 19, 2023

(54) SYSTEM FOR INTEGRATING MULTIPLE SENSOR DATA TO PREDICT A FALL RISK

(71) Applicant: Honeywell International Inc., Charlotte, NC (US)

(72) Inventors: Thomas Negre, San Jose, CA (US); Brad Rohlf, Minneapolis, MN (US); Praveen Sharma, Dublin, CA (US); Juan Noceda, Stoneham, MA (US)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 18 days.

This patent is subject to a terminal disclaimer.

(21) Appl. No.: 17/397,368

(22) Filed: Aug. 9, 2021

(65) Prior Publication Data

US 2021/0366258 A1 Nov. 25, 2021

Related U.S. Application Data

(63) Continuation of application No. 15/570,688, filed as application No. PCT/US2016/029517 on Apr. 27, 2016, now Pat. No. 11,120,679.

(Continued)

(51) Int. Cl.
*G08B 21/04* (2006.01)
*A62B 35/00* (2006.01)
(Continued)

(52) U.S. Cl.
CPC ...... *G08B 21/0446* (2013.01); *A62B 35/0025* (2013.01); *A62B 35/0043* (2013.01);
(Continued)

(58) Field of Classification Search
CPC .......................... G08B 21/0446; G08B 21/02; A62B 35/0025; A62B 35/0043; A62B 35/0075;
(Continued)

(56) References Cited

U.S. PATENT DOCUMENTS 4,571,320 A   2/1986   Walker
4,987,332 A   1/1991   Yamamoto et al.
(Continued)

FOREIGN PATENT DOCUMENTS

CA   2826700 A1   3/2014
CN   1977563 A    6/2007
(Continued)

OTHER PUBLICATIONS

A feasibility study of using smartphone built-in accelerometers to detect fall ports, "Automation in Construction", vol. 38, p. 74-86, (Ren-Jye Dzeng et al, Mar. 15, 2014.*
(Continued)

*Primary Examiner* — Quan Zhen Wang
*Assistant Examiner* — Mancil Littlejohn, Jr.
(74) *Attorney, Agent, or Firm* — ALSTON & BIRD LLP

(57) ABSTRACT

A method of determining the likelihood of a slip or fall comprises receiving, by a detection application stored in a non-transitory memory and executed on a processor, a plurality of sensor readings from a plurality of movement sensors, comparing, by the detection application, the plurality of sensor readings with a plurality of movement patterns stored in a database, determining, by the detection application, that at least one of the movement patterns of the plurality of movement patterns matches the plurality of sensor readings, and generating, by the detection application, an indication that a slip or fall is likely based on the plurality of sensor readings. The plurality of movement sensors is associated with different areas of a worker's body.

20 Claims, 4 Drawing Sheets

Related U.S. Application Data

(60) Provisional application No. 62/154,963, filed on Apr. 30, 2015.

(51) Int. Cl.
   *G01N 33/00*     (2006.01)
   *G01P 15/18*     (2013.01)
   *G06N 5/047*     (2023.01)

(52) U.S. Cl.
   CPC ...... *A62B 35/0075* (2013.01); *A62B 35/0093* (2013.01); *G01N 33/0004* (2013.01); *G01P 15/18* (2013.01); *G06N 5/047* (2013.01)

(58) Field of Classification Search
   CPC . A62B 35/0093; G01N 33/0004; G01P 15/18; G06N 5/047; G06Q 10/06398; G06Q 10/0635
   See application file for complete search history.

(56) References Cited

U.S. PATENT DOCUMENTS

| | | | |
|---|---|---|---|
| 6,675,130 | B2 | 1/2004 | Kanevsky et al. |
| 7,248,172 | B2* | 7/2007 | Clifford .................. G16H 40/67 340/573.7 |
| 11,120,679 | B2 | 9/2021 | Negre et al. |
| 2004/0097823 | A1 | 5/2004 | Friedrichs et al. |
| 2006/0001545 | A1* | 1/2006 | Wolf .................. G08B 21/0446 340/686.1 |
| 2006/0015032 | A1 | 1/2006 | Gordon |
| 2006/0109110 | A1* | 5/2006 | Hill ......................... G07C 9/28 340/539.13 |
| 2006/0252999 | A1* | 11/2006 | Devaul ................. A61B 5/0024 128/920 |
| 2007/0243869 | A1 | 10/2007 | Kwon et al. |
| 2007/0273504 | A1 | 11/2007 | Tran |
| 2007/0278830 | A1 | 12/2007 | Nakao |
| 2009/0201293 | A1 | 8/2009 | Tung et al. |
| 2012/0000731 | A1* | 1/2012 | Schienda .................. B66B 5/06 187/305 |
| 2013/0023798 | A1* | 1/2013 | Greene ................... A61B 5/112 600/595 |
| 2013/0332108 | A1 | 12/2013 | Patel |
| 2014/0126988 | A1 | 5/2014 | Qi et al. |
| 2014/0278830 | A1 | 9/2014 | Gagne |
| 2015/0014092 | A1 | 1/2015 | Blaise et al. |
| 2015/0027808 | A1 | 1/2015 | Baillargeon et al. |
| 2015/0123785 | A1* | 5/2015 | Haflinger ............. A61B 5/6822 340/539.11 |
| 2016/0120432 | A1* | 5/2016 | Sridhar .................... A61B 5/30 600/544 |

FOREIGN PATENT DOCUMENTS

| | | |
|---|---|---|
| CN | 101510114 A | 8/2009 |
| CN | 101641568 A | 2/2010 |
| CN | 103198615 A | 7/2013 |
| CN | 103366504 A | 10/2013 |
| CN | 103581852 A | 2/2014 |
| CN | 103932445 | 7/2014 |
| CN | 104504855 A | 4/2015 |
| CN | 204954848 U | 1/2016 |
| CN | 107444909 A | 12/2017 |
| CN | 107710293 A | 2/2018 |
| CN | 107745963 A | 3/2018 |
| CN | 207273223 U | 4/2018 |
| DE | 2357118 A1 | 5/1975 |
| EP | 2801318 A1 | 11/2014 |
| EP | 3289573 A2 | 3/2018 |
| EP | 3346402 A1 | 7/2018 |
| JP | 2000-006074 A | 1/2000 |
| JP | 2010-278408 A | 12/2010 |
| KR | 10-2011-0073172 A | 6/2011 |
| KR | 10-1259560 B1 | 4/2013 |
| KR | 10-2013-0081063 A | 7/2013 |
| WO | 2010/109923 A1 | 9/2010 |
| WO | 2010/144120 A2 | 12/2010 |
| WO | 2014/120893 A1 | 8/2014 |
| WO | 2016/176301 A2 | 11/2016 |

OTHER PUBLICATIONS

Advisory Action (PTOL-303) dated Oct. 17, 2019 for U.S. Appl. No. 15/570,688.
CN Notice of Allowance, including Supplemental Search Report, dated Jul. 13, 2021 for CN Application No. 201680038793, 5 pages.
CN Office Action dated Apr. 15, 2021 for CN Application No. 201680038793, 5 pages.
Communication about intention to grant a European patent dated Apr. 28, 2021 for EP Application No. 16731387, 5 pages.
Decision to grant a European patent received for European Application No. 16731387.3, dated Sep. 9, 2021, 2 pages.
Dzeng, Ren-Jye et al., A feasibility study of using smartphone built-in accelerometers to detect fall portents, Automation in Construction, vol. 38 (2014) pp. 74-86.
English translation of CN Notice of Allowance dated Jul. 13, 2021 for CN Application No. 201680038793, 3 pages.
English Translation of CN Office Action dated Apr. 15, 2021 for CN Application No. 201680038793, 5 pages.
Europe Patent Application No. EP16731387.3, Communication pursuant to Rules 16(11) and 162 EPC, dated Dec. 7, 2017, 3 pages.
Extended European search report dated Dec. 14, 2021 for EP Application No. 21189437, 10 pages.
Final Rejection dated Jun. 28, 2019 for U.S. Appl. No. 15/570,688.
Final Rejection dated Mar. 17, 2021 for U.S. Appl. No. 15/570,688.
IPEA/408—Written Opinion of the IPEA dated Dec. 23, 2016 for WO Application No. PCT/US16/029517.
IPEA/409—International Preliminary Report on Patentability dated Nov. 9, 2017 for WO Application No. PCT/US16/029517.
Non-Final Rejection dated Aug. 31, 2020 for U.S. Appl. No. 15/570,688.
Non-Final Rejection dated Jan. 27, 2020 for U.S. Appl. No. 15/570,688.
Non-Final Rejection dated Nov. 16, 2018 for U.S. Appl. No. 15/570,688.
Notice of Allowance and Fees Due (PTOL-85) dated Aug. 4, 2021 for U.S. Appl. No. 15/570,688.
Notice of Allowance and Fees Due (PTOL-85) dated May 12, 2021 for U.S. Appl. No. 15/570,688.
Notice of Allowance and Fees Due (PTOL-85) dated May 21, 2021 for U.S. Appl. No. 15/570,688.
Notice of Allowance received for U.S. Appl. No. 15/570,688, dated Aug. 4, 2021, 2 pages.
Office Action for Chinese Application 201680038793.3, dated Apr. 30, 2019, 6 pages [No English translation available].
Office Action for related Chinese Application No. 201680038793.3 dated Jan. 9, 2020, 19 pages.
Office Action for related CN Application No. 201680038793.3 dated Jul. 24, 2020, 18 pages.
Office Action received for European Patent Application No. 16731387.3, dated May 3, 2019, 4 pages.
Outgoing—ISA/210—International Search Report dated Dec. 23, 2016 for WO Application No. PCT/US16/029517.
CN Office Action, including Search Report, dated Aug. 19, 2022 for CN Application No. 202111037200, 13 pages.
English Translation of CN Office Action dated Aug. 19, 2022 for CN Application No. 202111037200, 12 pages.
CN Office Action dated Feb. 22, 2023 for CN Application No. 202111037200.
English Translation of CN Office Action dated Feb. 22, 2023 for CN Application No. 202111037200.

\* cited by examiner

SYSTEM FOR INTEGRATING MULTIPLE SENSOR DATA TO PREDICT A FALL RISK

CROSS-REFERENCE TO RELATED APPLICATIONS

This application is a continuation of U.S. patent application Ser. No. 15/570,688, filed Oct. 30, 2017 and entitled "System for Integrating Multiple Sensor Data to Predict a Fall Risk," which is a National Stage Entry of International Patent Application No. PCT/US16/29517, filed Apr. 27, 2016, which claims priority to and the benefit of U.S. Provisional Patent Application Ser. No. 62/154,963 filed on Apr. 30, 2015 and entitled "System for Integrating Multiple Sensor Data to Predict a Fall Risk," the entire disclosures of each of which are incorporated herein by reference in their entireties for all purposes.

BACKGROUND

A fall protection system may use multiple sensor inputs associated with a worker. Workers operating at heights can experience slips and falls that can result in injury to the workers. Passive safety systems such as restraint systems based on a fall velocity, safety lines having a fixed length, and the like can be used to prevent injury to workers in a fall situation. However, these systems may still allow a worker to fall a short distance prior to stopping the fall. Further, passive systems do not notify other workers of the fall situation.

SUMMARY

In an embodiment, a method of determining the likelihood of a slip or fall comprises receiving, by a detection application stored in a non-transitory memory and executed on a processor, a plurality of sensor readings from a plurality of movement sensors, comparing, by the detection application, the plurality of sensor readings with a plurality of movement patterns stored in a database, determining, by the detection application, that at least one of the movement patterns of the plurality of movement patterns matches the plurality of sensor readings, and generating, by the detection application, an indication that a slip or fall is likely based on the plurality of sensor readings. The plurality of movement sensors is associated with different areas of a worker's body.

In an embodiment, a method of determining the risk of a slip or fall comprises receiving, by a management application stored in a non-transitory memory and executed on a processor, specifications for a work event, identifying, by the management application, a first plurality of prior movement patterns associated with the specifications, receiving, by the management application, a plurality of sensor readings from a plurality of sensors associated with the location information, selecting a second plurality of prior movement patterns from the first plurality of movement patterns based on the plurality of sensor readings, and determining a slip or fall risk rating for the work event based on the second plurality of prior movement patterns. The specifications comprise location information, height information, and work requirements.

In an embodiment, a system for predicting a slip or fall comprises a plurality of movement sensors, and a receiver in signal communication with the plurality of movement sensors. The plurality of movement sensors are associated with different areas of a worker's body. The receiver comprises a memory and a processor, and the memory comprises a detection application that when executed on the processor, configures the processor to: receive a plurality of sensor readings from the plurality of movement sensors, compare the plurality of sensor readings with a plurality of stored movement patterns, determine that at least one of the movement patterns of the plurality of movement patterns matches the plurality of sensor readings, and generate a warning of a slip or fall based on the determination that the at least one of the movement patterns of the plurality of movement patterns matches the plurality of sensor readings.

These and other features will be more clearly understood from the following detailed description taken in conjunction with the accompanying drawings and claims.

BRIEF DESCRIPTION OF THE DRAWINGS

For a detailed description of the preferred embodiments of the invention, reference will now be made to the accompanying drawings in which.

DETAILED DESCRIPTION

Figure 1:
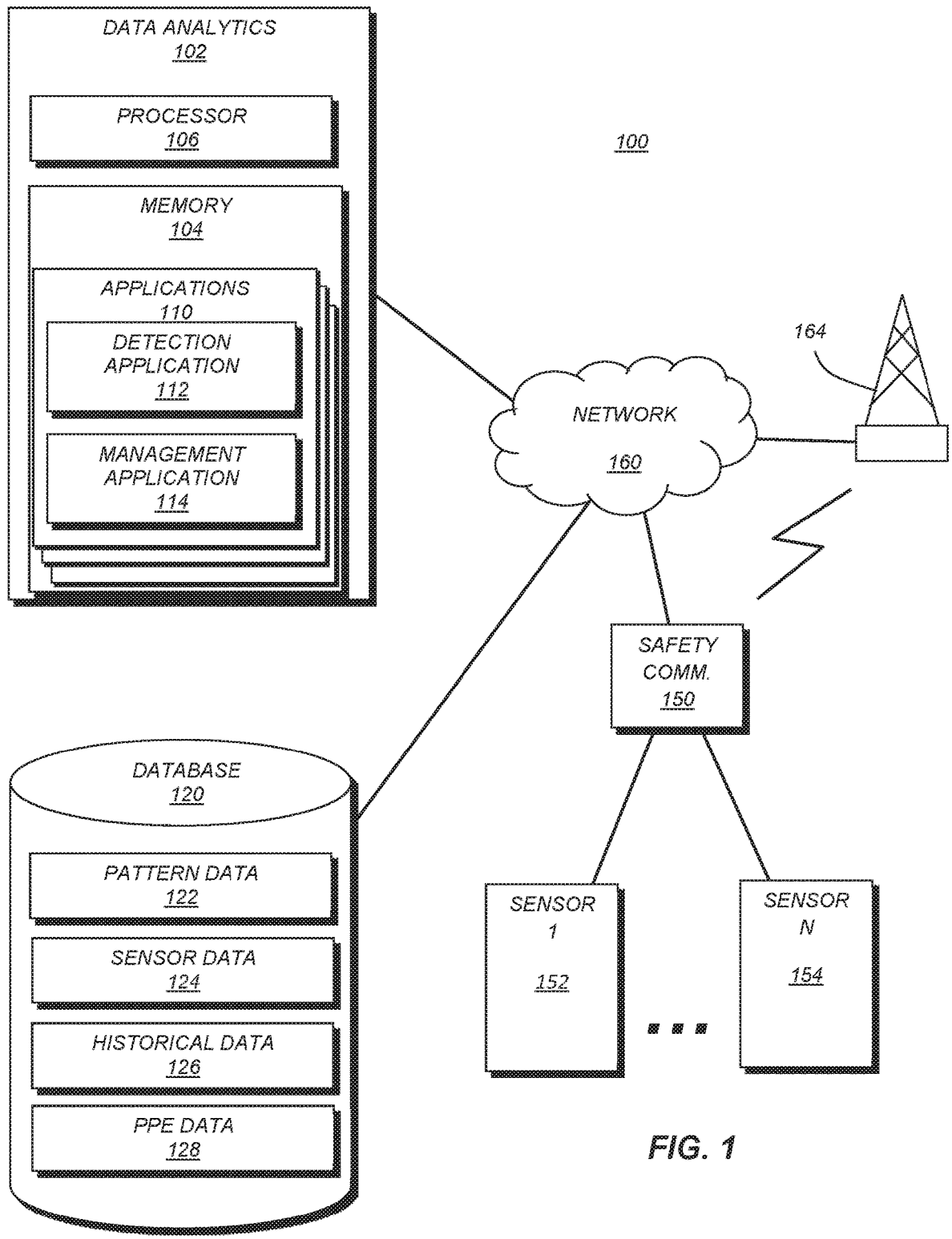
FIG. 1 is a schematic diagram of a multi-sensor system according to an embodiment.

It should be understood at the outset that although illustrative implementations of one or more embodiments are illustrated below, the disclosed devices, systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

In an embodiment, a workplace safety system may allow a plurality of sensors associated with environmental, location, movement, and biometric information to be used to provide an integrated safety solution for one or more workers. A number of sensors can be employed, and the data from the sensors can be combined to provide a better view of the personal safety of the workers. For example, data from fixed and/or mobile sensors can be used to detect the movement of a worker, chemical components of an environment, environmental conditions (e.g., temperature, pressure, wind speed, wind direction, etc.), vibration levels, noise levels, biometric parameters (e.g., heart rate, body temperature, respiration rate, etc.), location (e.g., including 2-dimensional and/or 3-dimensional position), and the like. The resulting data can be relayed through a communication module to a server, where the data can be combined to provide an overall view of a worker's risk factor. Various information such as alarms, notifications, information (e.g., maintenance protocols, instructions, live help, etc.), and the like can be relayed back to the worker through the system. The system may provide for better personal safety as a result of real time or near real time updates, improved productivity through the processing of multiple types of data, and better worker compliance with safety protocols by providing real time or near real time monitoring of personal protective equipment use, qualifications, and training for a variety of activities. All of these systems can provide feedback to the worker to improve productivity, compliance, and safety in ways that have not previously been as efficient.

Disclosed herein is an automated system for detecting slips and falls. The system can include sensors to provide for an automatic detection of a slip or fall and initiate various actions such as the use of restraint systems and the generation of warning signals to various personnel. The sensor used in the system can include accelerometers, altitude sensors (e.g., pressure sensors, etc.), location sensors, and the like. In some embodiments, a worker can have multiple sensors. For example, accelerometers can be located on the workers feet (e.g., in the worker's shoes, etc.), hands (e.g., in the worker's gloves, etc.), and other locations such as a harness measurement, which may provide a center of mass acceleration relative to the worker's hands and feet. The sensors may all be in communication with a single fall protection system or device, which may be associated with the worker. For example, a safety communicator comprising a non-transitory memory, a processor, and a communication system can be carried by the worker. The safety communicator can be in signal communication with each accelerometer or other sensor(s) to collect and process the sensor information. The safety communicator may also be in communication with a server over a wireless communication path.

Movements of the person can be matched to a database of known or expected patterns. For example, a normal climbing pattern could include a steady or periodic movement of the center of mass acceleration in a single direction. At the same time, the hands and feet may provide periodic movement in the same or similar direction. Such a combined pattern could be matched to an expected movement of the worker as the worker ascends or descends a structure. Various slip and fall patterns can also be developed for a worker or a group of workers to indicate when the worker may be experiencing a slip and/or a fall. For example, a sudden downward movement of a hand or foot relative to the other hands/feet and/or the center of mass measurement may indicate that the corresponding hand/foot has slipped. This may provide an initial warning that the worker has slipped. A fall may be indicated by a free-fall measurement of one or more hand/foot and/or the center of mass measurement. In this embodiment, the pattern may comprise a plurality of sensor inputs that can be measured as a group and/or as relative movements of the sensor inputs.

In order to detect the pattern, the sensor inputs may be continually measured and matched to a set of patterns. The patterns can be stored in a central memory location (e.g., on a server) and/or on the safety communicator associated with the worker. One or more of the patterns can indicate an expected climbing pattern (e.g., an ascent, a descent, a steady position for working, etc.). When an expected climbing pattern is detected, the system may continue to monitor the sensor inputs and/or provide an indication to the worker or other personnel that the worker is in a normal working state. When a pattern is detected that matches a slip and/or fall pattern, various alarms, notifications, and signals can be generated. For example, a signal to an automatic harness can be generated to stop the fall. An alert can also be sent to a supervisor or other personnel to indicate that the worker has fallen. In response to the detection of a fall, various other sensor data can be obtained. For example, biometric information for the worker can be obtained and sent to a supervisor or other personnel. A communication channel can be opened to the worker, for example through the safety communicator to check the status of the worker. Any of a variety of other sensors and actions can also be taken based on the slip and/or fall detection.

In some embodiments, the sensor inputs surrounding a slip or fall situation can be obtained and used to further refine or develop the patterns. In this embodiment, the sensor inputs surrounding a slip and/or fall can be collected and a learning algorithm can be used to detect the relative pattern of the various sensors during the slip and/or fall. The observed patterns can include the movements of the individual sensors, the relative movements of the sensors with respect to each other, the and the timing of the various movements with respect to each other, and the like. The resulting patterns can be added to a database of the patterns and used in future detection scenarios. In this way, an integrated fall protection system can be created that continuously monitors a worker and provides an improved safety system.

Referring to FIG. 1, a system 100 for providing workplace safety based on a combination of sensor inputs is illustrated. As shown in FIG. 1, the system may comprise a plurality of sensors 152, 154 in signal communication with a safety communicator 150. The safety communicator may provide a data connection to a data analytics server 102, a database 120 through a network 160. The safety communicator 150 may be wirelessly coupled to the network through an access point such as a wireless fidelity (Wi-Fi), Bluetooth, or cellular connection (e.g., through a wireless service tower 164).

In the system 100, the network 160 may be the internet representing a worldwide collection of networks and gateways that use the Transmission Control Protocol/Internet Protocol (TCP/IP) suite of protocols to communicate with one another. In some embodiments, the system 100 may also be implemented as a number of different types of networks such as, for example, an intranet, a local area network (LAN), or a wide area network (WAN). FIG. 1 is intended as an example and not as an architectural limitation for varying embodiments.

The data analytics server 102 can comprise a memory 104 (e.g., a non-transitory memory), a processor 106, and one or more applications 110 stored in the memory that can configure the processor 106 to perform certain functions. In general, the data analytics server 102 is configured to receive sensor data such as movement information for one or more portions of a worker's body, biometric data, environmental data, and/or location data associated with a worker and/or one or more sensors. The data analytics server 102 can process the data to provide information to the worker and/or decision makers at a facility. The data analytics server 102 is in communication with a database 120 that serves to store information used within the system 100. The database 120 can include a pattern data store 122, a sensor data store 124, a historical data store 126 and/or a personal protective equipment (PPE) store 128.

The applications 110 can include a detection application 112 and/or a management application 114. Each application can communicated with one or more of the sensors 152, 154 and/or the safety communicator 150. The detection application 112 can receive the sensor data and perform pattern matching based on the plurality of movement sensor measurements. The resulting analysis can be used to detect a slip or fall and provide information to the safety communicator 150. For example, the information can include alerts, notifications, information for performing a procedure, inputs (e.g., triggers, etc.) to safety devices (e.g., fall protection harness, etc.), or the like.

In an embodiment, the detection application 112 can receive a plurality of inputs from the sensors. As described in more detail below, the sensors can detect movement and/or position information associated with a worker, location information, environmental information, biometric information from a worker, noise levels, and the like. In an embodiment, the detection application 112 can be used to predict a risk for a slip and fall incident based on an expected activity and location. In some embodiments, the detection application 112 may execute on the safety communicator associated with a worker.

The sensor data can be stored in the sensor data store 124 and used with the system. In general, the sensor data can be used to determine various information about the worker. For example, movement sensors such as accelerometers can be coupled to one or more portions of the worker's body. The movement sensors can be located at or near a worker's hands, feet, torso, and/or head. In some embodiments, the movement sensor may be associated with the equipment used by the worker such as a safety harness or as a separate movement sensor clipped to the worker. The movement sensors may provide information on the movement of portions of the worker's body, which may provide information on the movements of the worker. In some embodiments, the movement sensors can sense an orientation of the worker, which may also be part of the pattern information. For example, a reading that a worker is upside down, lying flat, or leaning at an angle may be part of the pattern of a slip and fall. Additional sensor outputs including a geolocation output, a height output, and biometric output can also be used to characterize the worker's location and movements.

The detection application 112 can use the sensor data directly from the sensors 152, 154, and/or rely on sensor data stored in the sensor data store 124. The detection application 112 is generally configured to use the sensor data to determine a movement pattern of the worker as the worker is moving within a facility. Various patterns can be detected. For example, the worker may be ascending a structure, descending a structure, working at a fixed location, moving within a facility, or performing a variety of other activities. The detection application 112 may develop patterns by recording the sensor outputs during various types of activities and determining characteristics of the sensor outputs individually and/or relative relationships among the sensor readings. For example, a sudden downward movement of a hand or foot relative to the other hands/feet and/or the center of mass measurement may indicate that the corresponding hand/foot has slipped. This may provide an initial warning that the worker has slipped. In other cases, the movement sensors may detect that the worker is at an angle that may result in a fall. A fall may be indicated by a free-fall measurement of one or more hand/foot and/or the center of mass measurement. Other patterns to characterize regular ascents, descents, movements, orientations, and the like can also be determined in order to characterize the worker's movements at any given time.

In some embodiments, the pattern of movements leading up to a slip or fall can be determined. While these activities may include normal movement, a pattern of regular movements that lead to common slip and fall scenarios can be detected. For example, a simultaneous movement of two or three limbs may indicate that a fall is likely. Similarly, an orientation reading that indicates that a worker is leaning over may indicate that a fall is likely in some types of activities. Other patterns can also be determined, and the patterns may be specific to certain types of activities. The patterns can be stored in the pattern data store 122 in a variety of formats. For example, the patterns or representations of the patterns can be stored in the pattern data store 122. When learning algorithms are used, the model parameters and weights can be stored as an indication of the patterns. Other suitable representations of the pattern data can also be used, alone or in combination with other parameters as described herein.

In some embodiments, the pattern of movements can be determined using actual tests. In an embodiment, a worker can be outfitted with a plurality of sensors such as a plurality of movement sensors (e.g., accelerometers, etc.) and perform a variety of expected movements. For example, a worker with accelerometers associated with their hands and feet, and optionally their center of mass (e.g., on a chest harness or strap), can climb a ladder, climb a tower, descend a side of a building, lean out to perform a task, or the like. A plurality of initial tests can be conducted and the movement patterns can be recorded in the pattern data store 122 to allow the recorded patterns to be used for matching and/or training of various learning algorithms. In addition, accident patterns can be modeled or predicted (e.g., acted out), and the results can be recorded and stored to provide patterns for matching to slip and fall data and/or used as training data for various learning algorithms. In some embodiments, the patterns leading up to a slip and/or fall can be separately extracted to allow the movement patterns leading to a fall to be matched and/or modeled. This information may be used to predict a slip and/or fall prior to the slip and/or fall occurring.

Figure 2:
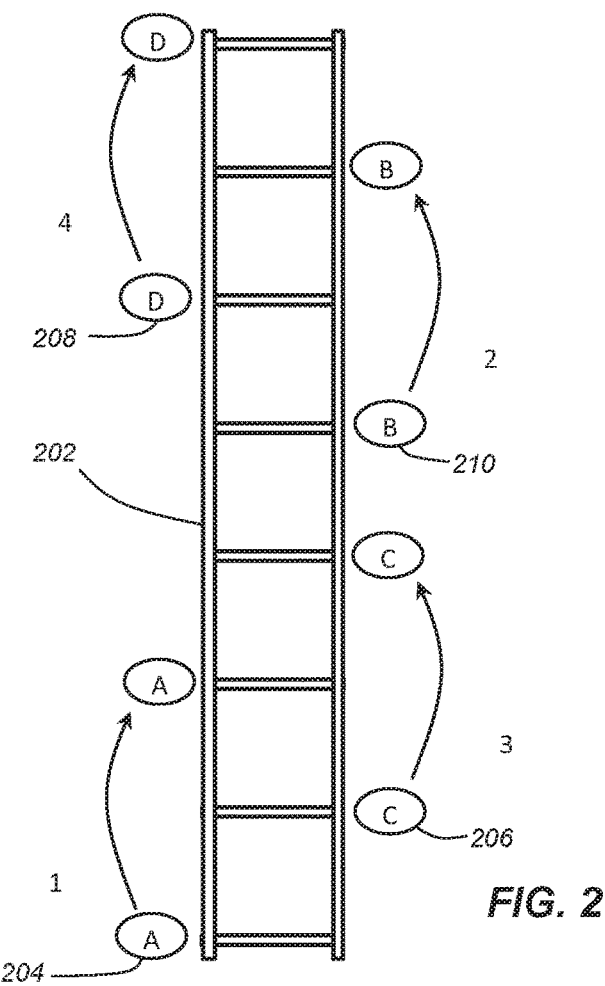
FIG. 2 is a schematic view of a climbing surface and a pattern of movement according to an embodiment.
Figure 3:
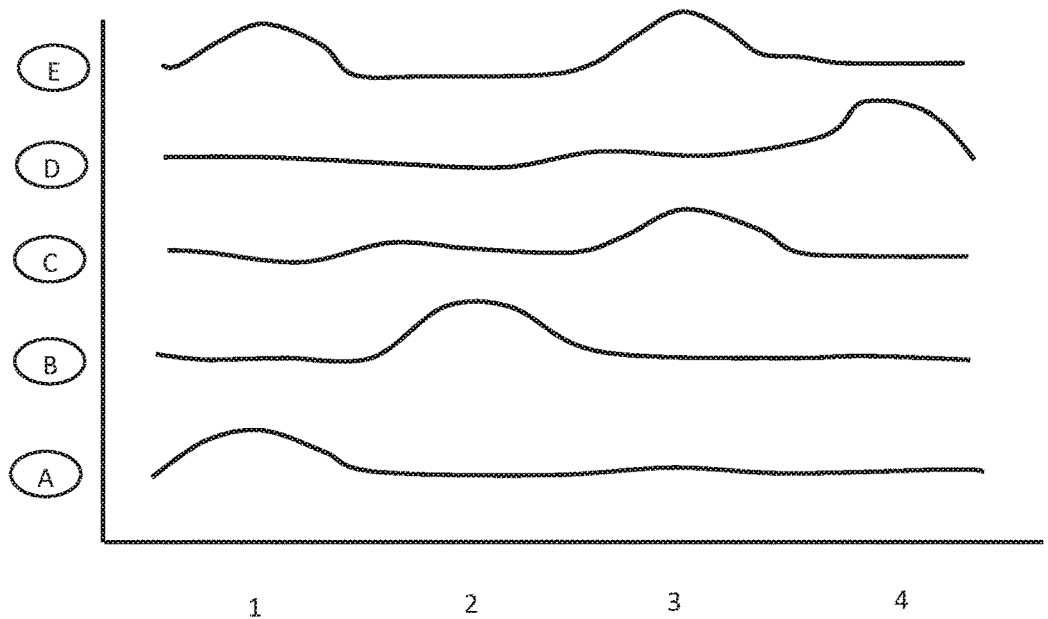
FIG. 3 is a schematic illustration of a plurality of outputs of a plurality of movement sensors that together form a movement pattern according to an embodiment.

An exemplary embodiment of a movement pattern is schematically illustrated in FIGS. 2 and 3. FIG. 2 schematically illustrates a hand and foot pattern for climbing a ladder 202. As shown the left foot 204 is indicated by the letter "A," the right foot 206 is indicated by the letter "C," the right hand 210 is indicated by the letter "B," and the left hand 208 is indicated by the letter "D." A climbing pattern is generally indicated by the numbered sequence 1 through 4. Initially, the left foot 204 may move from a lower rung to a higher rung. Safe climbing techniques may provide that the other three points of contact remain fixed so that there are three points of contact with the climbing surface at all times. Once the left foot has moved to the position indicated by the lower "A" to the upper "A," the right hand 210 may be moved from a lower rung to a higher rung as indicated by the arrow between the B positions. As a third step, the right foot 206 may be moved from a lower rung to a higher rung as indicated by the arrow between the C positions. Finally, the left hand 208 may be moved from a lower rung to a higher rung as indicated by the arrow between the D positions. This process may then be repeated starting with the A positions as the worker moves higher up the climbing surface such as ladder 202.

The expected movement patterns as indicated in two dimensions by a suitable movement sensor (e.g., an accelerometer(s), etc.) are shown in FIG. 3 for this process. In step 1, an upwards movement is indicated by a movement sensor associated with the left foot. During the remainder of the cycle, there may be some minor movement of the left foot 204 as other bodily movements are made, but the movement sensor will generally have an output that is relatively stable and does not exceed a threshold either up or down. At the second step, the movement sensor associated with the right hand will provide a sensor output indicating an upward movement. During the remainder of the cycle, the movement sensor output for the movement sensor associated with the right hand is expected to be less than a threshold. At the third step, the movement sensor associated with the right foot 206 will provide a sensor output indicating an upward movement. During the remainder of the cycle, the movement sensor output for the movement sensor associated with the right foot is expected to be less than a threshold. Finally, at the fourth step in the climbing cycle, the movement sensor associated with the left hand will provide a sensor output indicating an upward movement. During the remainder of the cycle, the movement sensor output for the movement sensor associated with the left hand is expected to be less than a threshold.

In addition to the movement sensors associated with a workers feet and/or hands, a center of mass movement sensor can also be used. The movement associated with such a sensor is shown as sensor "E" in FIG. 3. The center of mass measurement may generally move when the body of the worker is lifted by the movement of the worker's legs as would generally be expected to occur at or near the time the worker's feet move. As a result, an upwards movement may be expected during the first and third steps of the movement cycle as shown by the center of mass sensor outputs indicating an upward movement approximately during the first and third steps of the movement cycles. It can be noted that the ascending climbing pattern includes movements associated with a plurality of movement sensors and can include information that associates the relative movement times (e.g., the right hand sensor is expected to indicate an upward movement after the left foot has become stationary, etc.) and expected combinations of movements (e.g., the center of mass moves with the left and right feet, the center of mass does not move with the left or right hand, etc.). Such a pattern and combination of movements may be used to identify various movement patterns to specific activities. Once obtained, the pattern resulting from the climbing cycle shown in FIG. 2 could then be recorded in the pattern data store 122 for use in matching an ascending climbing pattern or for use as training data in a learning algorithm.

Figure 4:
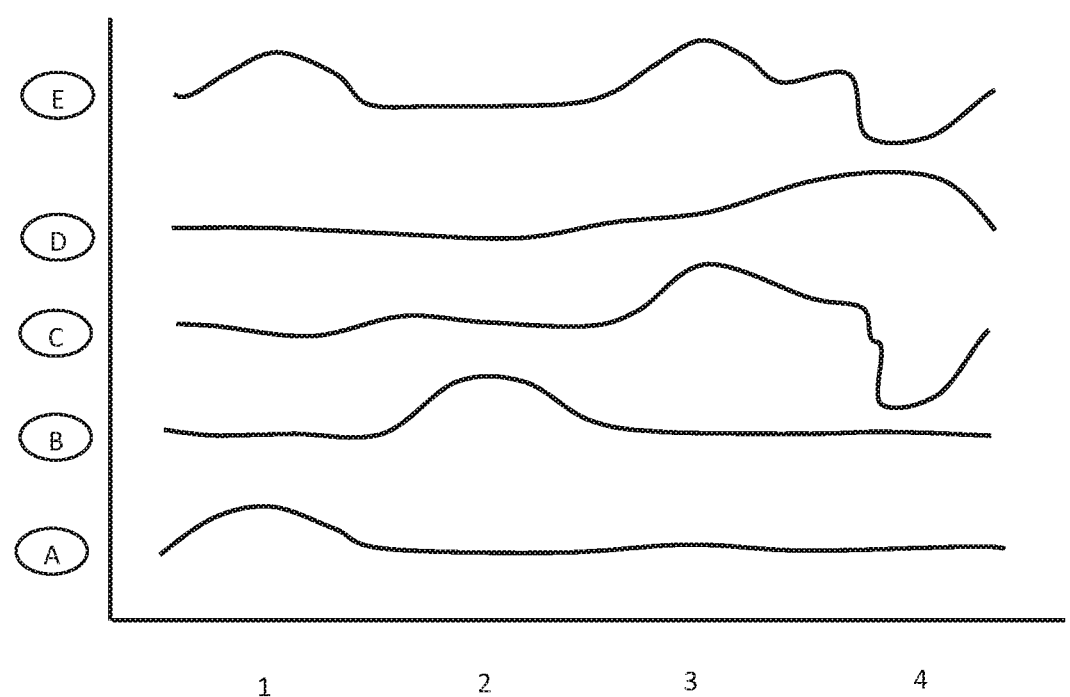
FIG. 4 is another schematic illustration of a plurality of outputs of a plurality of movement sensors that together form a movement pattern according to an embodiment.

An additional movement pattern is schematically illustrated in FIG. 4. As illustrated, the movement patterns generally follow those shown in FIG. 3. The main difference is the downward movement indicated by sensor C (the right foot 206 of FIG. 2 (during the fourth step in the ascending movement cycle. The sudden downward movement indicated by the relatively fast or sharp downward movement may indicate that the right foot has slipped while the left hand is moving upwards. It can also be seen that the movement of the left hand (e.g., as indicated by sensor "D") begins to move upwards before the movement of the right foot is stationary. Such a pattern may indicate that two points of contact are moving at the same time. The movement patterns also indicate that the center of mass movement sensor also follows the movement of the right foot and illustrates a downward movement that matches the movement of the right foot. Thus, the pattern illustrated in FIG. 4 can be recorded and stored in the pattern data store 122. This pattern may then be used to match a slip and/or fall pattern and/or train a learning algorithm to identify a slip and/or fall. The movement pattern illustrated in FIG. 4 may also be used to identify a situation leading up to a slip and/or fall. For example, the pattern may be used to identify the relative movement outputs of the various movement sensors prior to the slip occurring. In this example, such an indicator may be provided by the simultaneous movement of two of the four movement sensors associated with the hands and feet of the worker.

The patterns can also be classified or correlated with a various types of additional information such as location, environmental conditions, biometric information, type of activity, and the like. For example, various locations require climbing at a facility can be individually considered in determining patterns. The results may provide specific movement patterns at specific locations that lead to slips and falls. Other conditions such as environmental conditions, (e.g., wind speed, temperature, precipitation, etc.) may also be take into account in the pattern recognition process. For example, slip and fall patterns can be analyzed during various temperature ranges and/or under certain precipitation conditions. Still further, various biometric conditions can be used to further categorize the patterns. For example, patterns can be developed for a worker having a high heart rate or exhibiting signs of an illness relative to a normal biometric pattern. This may allow for identification of conditions under which slips and falls are likely to occur as well as any differences in movement patterns between the various types of categories. This may allow for extra precautions to be taken at certain locations, under certain circumstances, or with certain types of activities.

In some embodiments, the patterns can be classified by the type of activity. Different activities can be expected to involve different types of movement. In some types of activities, the movement patterns may not result in slips and falls while in other activities, the same movement patterns may indicate that a slip and fall has taken place. For example, a worker in an offshore platform may be required to perform various actions involve leaning over, crawling under certain equipment, laying down, and climbing certain structures. The resulting patterns can be compared to a worker climbing wind turbine towers for repair. In a tower climbing example, any leaning over or inverted positions may be interpreted as having a high risk of a fall or having already fallen. If the same patterns were used, the platform worker may experience false alarms that could impede the performance of their work. Thus, the patterns can be classified by activity to allow for different patterns and movements that are specific to different types of work.

The safety communicator 150 may interact with one or more sensors to provide the information to the system 100. The sensors can include sensors associated with an individual and/or facility sensors. In general, the individuals may wear one or more personal protection equipment (PPE) devices for detection and communication. The movement sensors can be associated with the PPE. For example, gloves may incorporate an accelerometer to detect movement in the hands of the worker. Similar, boots may incorporate an accelerometer to indicate the movement of the worker's feet. A safety harness may comprise an accelerometer to detect the movement of the center of mass of the worker. Other biometric parameters may also be measured by the safety harness such as heart rate, body temperature, and the like. The safety communicator may comprise various sensors such as location sensor (e.g., a GPS sensor, triangulation sensor, etc.), altimeter, environmental sensors, and the like. In some embodiments, the movement sensors can be individual sensors that are attached to the worker in a desired position.

Other sensors may also be present. For example, a person may wear a portable chemical detector operable to identify gases in the air and determine the levels of chemicals in the environment. The sensors can detect various types of information such as chemical components of an environment, environmental conditions (e.g., temperature, pressure, wind speed, wind direction, etc.), vibration levels, noise levels, biometric parameters (e.g., heart rate, body temperature, respiration rate, etc.), location (e.g., including 2-dimension and/or 3-dimensional position), and the like. The chemical sensors can be detected using various types of gas sensors.

In some embodiments, the presence of the various environmental conditions such as chemicals may be correlated to the movement patterns to predict a slip and/or fall. For example, the presence and/or concentration of a certain chemical may be associated with reduced motor skills that can result in slips and/or falls. A worker exposed to certain chemicals may be more closely monitored or warned not to climb or perform work at height based on the environmental exposure in some circumstances.

Also, a person may wear any number of monitoring devices that may monitor movement, activity, breathing, heart rate, etc. Additionally, personnel may wear portable location devices operable to communicate the location of the device (and therefore the user) to a central monitoring station. These portable devices may communicate wirelessly, over a wireless fidelity (Wi-Fi) network, via Bluetooth, or another wireless connection.

Facility sensors, which may be stationary within a facility, may also be present. The stationary sensors can measure any of the information that the portable and personal sensors can measure. The stationary sensors may also measure information such as environmental data (e.g., pressure, temperature, wind speed, wind direction, precipitation, etc.). The facility sensors may communicate wirelessly and/or through a wired connection to the data analytics server 102 and/or the safety communicator 150 to provide data used with the applications 110.

In some cases, the multiple PPE devices associated with an individual may have alarms, notifications, or updates that are communicated to the user via sounds, vibrations, or visual notifications. In some embodiments, each PPE device may communicate individually with the central monitoring station, employing multiple wireless infrastructures. In some embodiments, a safety communicator 150 (e.g., a communication device) comprising a data collection and communication application may be used to collect the sensor data and communicate the sensor data to the various elements of the system 100. For example, the application may establish a connection between the smartphone and each of the PPE devices, which may be wireless connections, such as Wi-Fi or Bluetooth. The application may then receive data from each of the PPE devices, and store the data locally on the device. The application may also transfer the data to a cloud storage network via a cellular network. Additionally, the application may communication the combined data from all of the PPE devices to the central monitoring station. The application may automatically receive data from the PPE devices and send the data to the data analytics server 102. Additionally, the application may be operable to send messages or calls to other safety communicators associated with other individuals if needed, such as in an alarm or emergency situation.

The application on the safety communicator 150 may present information to the user via a user interface on the smartphone or connected to the smartphone (such as a smartwatch). The interface may compile the information received from each of the PPE devices into a consistent format, making it easier to read and understand. The user may be able to adjust alarm limits and settings in the application. The application may show real-time readings via the user interface, and may issue alerts or warnings via the user interface. Additionally, vibrations, audible alerts, or visual indications (e.g., flashing lights, etc.) may also be issued by the application via the smartphone. In some cases, the application may be operable to communicate with a headset or earpiece (such as a Bluetooth headset for example) worn by the user to communicate audible alerts or warnings.

The pattern information related to slips and falls can be stored in the pattern data store 122. The pattern information can be used to determine and/or predict potential slip and fall situations based on the patterns of movement themselves, and/or various types of learning algorithms can be used to indicate slip and fall situations. For example, statistical models, neural networks, and the like can be used to receive the patterns in the pattern data store 122 and create a model for matching the patterns to specific sensor readings. In some embodiments, base training sets can be predicted and/or obtained using real world data that are associated with various outcomes. The models may be used to extend the application of the patterns beyond those of the explicitly measured activity based patterns. The model, the model parameters, and various other information used with such models can be stored in the pattern data store 122 and used by the detection application 112.

In some embodiments, the detection application 112 can operate on the safety communicator 150 in order to provide real time or near real time information on the occurrence or potential for slip and fall movements. In this embodiment, the patterns and/or model and parameters can be sent to the safety communicator 150 at various intervals to allow the detection application 112 to operate on the safety communicator 150. By having the detection application 112 operate on the safety communicator 150, slip and fall movements and/or potential slip and fall movements can be determined in real time or near real time even if a network communication link is not present.

During use of the system, the sensor readings from each of the one or more sensors 152, 154 (e.g., a plurality of accelerometers associated with the hands, feet, and/or center of mass of a worker, etc.) can be received and used by the safety communicator 150 and/or the detection application 112 on the data analytics server 102 to determine the movements of the worker. The context in which the worker is present may optionally be detected and used with the detection application 112 in perform the pattern matching. For example, the detection of an ascending climbing pattern may allow the template ascending patterns and ascending slip and/or fall movement predictors to be filtered from the overall store of patterns in the pattern data store 122. Other pattern classifications such as descending climbing patterns, rope climbing, working at height and/or angles, can also be used to limit and or filter the patterns used in the matching process. The detection application 112 may first determine a movement pattern for the worker based on the readings from the sensors. The measured movement pattern can then be compared to one or more stored patterns to determine if the worker's movements represent a slip or fall and/or if the worker is experiencing a movement patter than has a high likelihood of resulting in a slip or fall. For example, a stored movement pattern representing a worker's movements prior to a slip and/or fall can be matched against the current movement pattern to predict that a slip and/or fall has a high likelihood of occurring. The pattern data used to match the worker's movement pattern can be obtained from the pattern data store 122. The pattern data may be obtained based on the context of the worker such as the location, type of activity, environmental conditions, and the like. In some embodiments, conditions beyond movement sensor outputs can be used in the analysis to predict the likelihood of a slip and/or fall based on a current movement pattern.

When the detection application 112 indicates that a worker is experiencing a movement pattern that has a high likelihood of resulting in a slip or fall, an alert, an alarm, a notification, and/or information (e.g., maintenance protocols, instructions, live help, etc.), and the like can be relayed back to the worker through the system. For example, the data analytics server 102 may send a message to the safety communicator 150 to display the information. The alerts can indicate the level of risk, a notification that additional PPE is required, or an indication that the individual should not continue the present activity, or proceed with caution. The ability to receive the sensor data and determine the slip and fall risk in real time or near real time may provide for better personal safety as a result of real time or near real time updates, improved productivity through the processing of multiple types of data, and better worker compliance with safety protocols by providing real time or near real time monitoring of personal protective equipment use, qualifications, and training for a variety of activities.

In some situations, the detection application 112 may determine that the movement pattern of a worker matches a slip and/or fall pattern. The indication may result in an alert, an alarm, a notification, or the like being issued to the worker and/or a supervisor. In addition, one or more actions can be performed based on the determination. For example, a warning can be sent to the worker and/or a safety harness can be activated to prevent a fall. Various other safety information can also be activated based on the determination that a slip or fall has occurred.

In an embodiment, a safety harness or lifeline such as a self-retracting lifeline can be activated based on the determination that a slip or fall has occurred, or in some embodiments, that a risk that a slip or fall is about to occur exceeds a threshold. For example, a self-retracting lifeline may comprise a engagement member that engages the line to prevent further movement of the line coupled to the worker. The safety communicator and/or the data analytics server 102 can communicate with the self-retracting lifeline and activate the engagement member. This may occur faster than a mechanical engagement of the engagement member that may occur based on a rapid movement of the support line. As a result, a worker may fall a shorter distance than if a purely mechanical activation were relied up.

In some embodiments, the actions taken based on detecting the various patterns can be based on a tiered notice schedule. As a first tier, the system may sent a message or alert based on a movement pattern that can result in a slip and/or fall. If the movement pattern continues to match or move towards a slip or fall situation, a second tier of notification can be issued. Alternatively, an action such as initiating a self-retracting lifeline can be taken to prevent the fall. The use of a tiered approach may allow for corrective action to be taken without fully engaging a safety system, which may reduce the occurrence of unnecessary activations of the safety equipment.

In an embodiment, the ability to predict a slip or fall based on the current movement patterns of a worker allows for a warning or message to be sent to the worker. For example, a vibration, sound, light, or other indicator may be sent to the worker to indicate that the current movement pattern matches a potential slip or fall situation. A similar warning may be sent to a management component to indicate that the worker is experiencing a potential slip or fall situation.

In some embodiments, a learning algorithm may be used to update the patterns in the pattern data store 122. Over time, and regardless of where the detection application executes, the sensor readings from the sensors 152, 154 can be stored in the sensor data store 124. In addition to the data from the sensors, the sensor data store 124 can include sensor readings for the facility from additional sensors or inputs such as from a plurality of workers. The detection application 112 may periodically use the sensor data from the sensors 152, 154 in combination with the data from other sensors to perform an analysis of the sensor readings including the movement readings as well as other readings such as location readings, environmental condition readings, biometric readings, and the like to update the existing patterns and/or develop new patterns. The new patterns can include patterns for new movements or circumstances that may not have been previously encountered. In addition, when a slip and/or fall occurs, the movement patterns can be recorded and stored in the pattern data store 122. The slip and/or fall patterns can be used to provide training data sets from real experiences to help the system identify actual slip and/or fall movement patterns. In addition, the movement patterns leading up to a slip and/or fall can be extracted and analyzed to identify the risks associated with a particular pattern and predict the risk of such a movement pattern. Similar patterns that are present in non-slip and/or non-fall situations can also be analyzed.

In some embodiments, a slip and/or fall pattern can be analyzed to determine the predicting pattern resulting in the slip and/or fall. For example, the exemplary slip and fall pattern shown in FIG. 4 can be analyzed, and the system may determine that simultaneous movement of one hand and one foot led to the slip and fall in the overall movement pattern. The system may then search the historical data store 126 for similar patterns. The percentage of times that the predicting pattern appears can be used to provide the risk rating for such a predicting pattern of movement. For example, if such a movement pattern results in a slip and/or fall over 80% of the time, such a movement pattern may be labeled a high risk. When such a pattern is detected, a warning may be initiated for the user and a safety device may trigger (e.g., a harness pre-tensioner may initiate, etc.). Other risks may trigger different warnings based on the analysis of past event data matching similar patterns. Such risks may also be sub-categorized based on other factors. For example, the environmental parameters and/or chemical concentrations can be used with the slip and/or fall prediction to subcategorize and/or provide learning information training sets for learning algorithms to provide multi-sensor inputs for predicting slips and/or falls.

In some embodiments, the updated analysis may be performed using data from across various facilities. For example, a sensor manufacturer may collect sensor readings including movement sensors such as accelerometers and other sensors such environmental condition sensors, gas sensors, biometric sensors, and the like across multiple facilities and use the detection application 112 to perform a pattern update. The resulting update can then be sent to one or more facilities using the respective sensors. The updated analysis can be performed continuously, periodically, and/or at discrete times.

When the patterns are updated, the updated patterns can be stored in the pattern data store 122. When the exposure application executes on local device such as the safety communicator, the patterns can be sent to the safety communicator for performing the cross-interference analysis. This may allow for an improved determination of the potential for slip and fall situations as well as recognition of actual slip and fall situations based on sensor readings.

In some embodiments, the management application 114 may execute based on expected job specifications. The management application 114 may interact with the detection application 112 to provide an estimate of the potential for a slip and fall situation based on the job parameters. For example, the job location, weather conditions, prior slip and fall situations associated with the job location, and the like can be taken into account to determine a potential slip and fall prediction or risk rating for a particular job. Various rules and/or policies can be used to specify the parameters for an activity.

The resulting determination by the management application 114 may be used to proactively specify safety standards or conditions. For example, the risk rating may provide recommendations on the PPE required, which may change based on the conditions and expected movements. As another example, the management application 114 may determine that a different worker should perform the job based on experience of training. In some embodiments, the management application 114 may provide a notification that the job should not be performed until one or more conditions change due to an excess slip and fall risk. For example, a management application 114 may indicate that a job that is to be performed at height should not be performed when the temperature is below freezing due to the potential slip and fall risks associated with the potential presence of ice on the climbing structures. In this manner, the detection application 112 and the management application 114 may be used to proactively provide a slip and fall risk rating based on patterns associated with slip and fall movements as well as considerations of other conditions expected for a movement at height. The risk rating can include a numerical value or another type of rating. For example, a green, yellow, red rating can be used to indicate a low, medium, or high risk for the activities. Since the management application 114 can include information for specific workers (e.g., training, certifications, etc.). the management application 114 can generate worker specific risk ratings.

Figure 5:
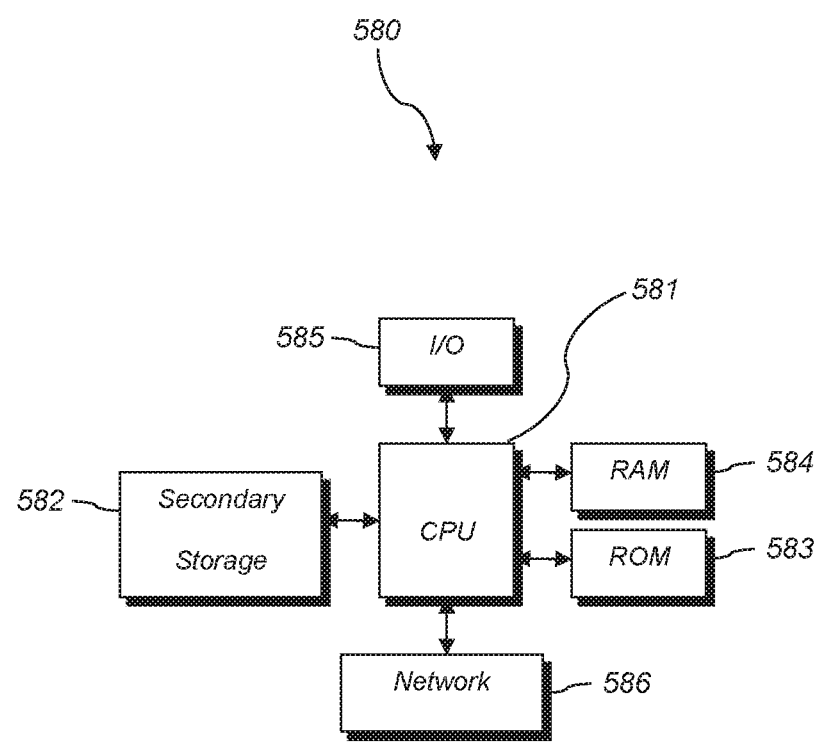
FIG. 5 schematically illustrates a computer that can be used to carry out various steps according to an embodiment.

Any of the systems and methods disclosed herein can be carried out on a computer or other device comprising a processor, such as the communication device 150, the data analytics server 102, any of the sensors 152, 154, and/or the database 120 of FIG. 1. FIG. 5 illustrates a computer system 580 suitable for implementing one or more embodiments disclosed herein such as the acquisition device or any portion thereof. The computer system 580 includes a processor 582 (which may be referred to as a central processor unit or CPU) that is in communication with memory devices including secondary storage 584, read only memory (ROM) 586, random access memory (RAM) 588, input/output (I/O) devices 590, and network connectivity devices 592. The processor 582 may be implemented as one or more CPU chips.

It is understood that by programming and/or loading executable instructions onto the computer system 580, at least one of the CPU 582, the RAM 588, and the ROM 586 are changed, transforming the computer system 580 in part into a particular machine or apparatus having the novel functionality taught by the present disclosure. It is fundamental to the electrical engineering and software engineering arts that functionality that can be implemented by loading executable software into a computer can be converted to a hardware implementation by well-known design rules. Decisions between implementing a concept in software versus hardware typically hinge on considerations of stability of the design and numbers of units to be produced rather than any issues involved in translating from the software domain to the hardware domain. Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example in an application specific integrated circuit (ASIC), because for large production runs the hardware implementation may be less expensive than the software implementation. Often a design may be developed and tested in a software form and later transformed, by well-known design rules, to an equivalent hardware implementation in an application specific integrated circuit that hardwires the instructions of the software. In the same manner as a machine controlled by a new ASIC is a particular machine or apparatus, likewise a computer that has been programmed and/or loaded with executable instructions may be viewed as a particular machine or apparatus.

Additionally, after the system 580 is turned on or booted, the CPU 582 may execute a computer program or application. For example, the CPU 582 may execute software or firmware stored in the ROM 586 or stored in the RAM 588. In some cases, on boot and/or when the application is initiated, the CPU 582 may copy the application or portions of the application from the secondary storage 584 to the RAM 588 or to memory space within the CPU 582 itself, and the CPU 582 may then execute instructions that the application is comprised of In some cases, the CPU 582 may copy the application or portions of the application from memory accessed via the network connectivity devices 592 or via the I/O devices 590 to the RAM 588 or to memory space within the CPU 582, and the CPU 582 may then execute instructions that the application is comprised of. During execution, an application may load instructions into the CPU 582, for example load some of the instructions of the application into a cache of the CPU 582. In some contexts, an application that is executed may be said to configure the CPU 582 to do something, e.g., to configure the CPU 582 to perform the function or functions promoted by the subject application. When the CPU 582 is configured in this way by the application, the CPU 582 becomes a specific purpose computer or a specific purpose machine.

The secondary storage 584 is typically comprised of one or more disk drives or tape drives and is used for non-volatile storage of data and as an over-flow data storage device if RAM 588 is not large enough to hold all working data. Secondary storage 584 may be used to store programs which are loaded into RAM 588 when such programs are selected for execution. The ROM 586 is used to store instructions and perhaps data which are read during program execution. ROM 586 is a non-volatile memory device which typically has a small memory capacity relative to the larger memory capacity of secondary storage 584. The RAM 588 is used to store volatile data and perhaps to store instructions. Access to both ROM 586 and RAM 588 is typically faster than to secondary storage 584. The secondary storage 584, the RAM 588, and/or the ROM 586 may be referred to in some contexts as computer readable storage media and/or non-transitory computer readable media.

I/O devices 590 may include printers, video monitors, liquid crystal displays (LCDs), touch screen displays, keyboards, keypads, switches, dials, mice, track balls, voice recognizers, card readers, paper tape readers, or other well-known input devices.

The network connectivity devices 592 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards that promote radio communications using protocols such as code division multiple access (CDMA), global system for mobile communications (GSM), long-term evolution (LTE), worldwide interoperability for microwave access (WiMAX), near field communications (NFC), radio frequency identity (RFID), and/or other air interface protocol radio transceiver cards, and other well-known network devices. These network connectivity devices 592 may enable the processor 582 to communicate with the Internet or one or more intranets. With such a network connection, it is contemplated that the processor 582 might receive information from the network, or might output information to the network (e.g., to an event database) in the course of performing the above-described method steps. Such information, which is often represented as a sequence of instructions to be executed using processor 582, may be received from and outputted to the network, for example, in the form of a computer data signal embodied in a carrier wave.

Such information, which may include data or instructions to be executed using processor 582 for example, may be received from and outputted to the network, for example, in the form of a computer data baseband signal or signal embodied in a carrier wave. The baseband signal or signal embedded in the carrier wave, or other types of signals currently used or hereafter developed, may be generated according to several methods well-known to one skilled in the art. The baseband signal and/or signal embedded in the carrier wave may be referred to in some contexts as a transitory signal.

The processor 582 executes instructions, codes, computer programs, scripts which it accesses from hard disk, floppy disk, optical disk (these various disk based systems may all be considered secondary storage 584), flash drive, ROM 586, RAM 588, or the network connectivity devices 592. While only one processor 582 is shown, multiple processors may be present. Thus, while instructions may be discussed as executed by a processor, the instructions may be executed simultaneously, serially, or otherwise executed by one or multiple processors. Instructions, codes, computer programs, scripts, and/or data that may be accessed from the secondary storage 584, for example, hard drives, floppy disks, optical disks, and/or other device, the ROM 586, and/or the RAM 588 may be referred to in some contexts as non-transitory instructions and/or non-transitory information.

In an embodiment, the computer system 580 may comprise two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an embodiment, virtualization software may be employed by the computer system 580 to provide the functionality of a number of servers that is not directly bound to the number of computers in the computer system 580. For example, virtualization software may provide twenty virtual servers on four physical computers. In an embodiment, the functionality disclosed above may be provided by executing the application and/or applications in a cloud computing environment. Cloud computing may comprise providing computing services via a network connection using dynamically scalable computing resources. Cloud computing may be supported, at least in part, by virtualization software. A cloud computing environment may be established by an enterprise and/or may be hired on an as-needed basis from a third party provider. Some cloud computing environments may comprise cloud computing resources owned and operated by the enterprise as well as cloud computing resources hired and/or leased from a third party provider.

In an embodiment, some or all of the functionality disclosed above may be provided as a computer program product. The computer program product may comprise one or more computer readable storage medium having computer usable program code embodied therein to implement the functionality disclosed above. The computer program product may comprise data structures, executable instructions, and other computer usable program code. The computer program product may be embodied in removable computer storage media and/or non-removable computer storage media. The removable computer readable storage medium may comprise, without limitation, a paper tape, a magnetic tape, magnetic disk, an optical disk, a solid state memory chip, for example analog magnetic tape, compact disk read only memory (CD-ROM) disks, floppy disks, jump drives, digital cards, multimedia cards, and others. The computer program product may be suitable for loading, by the computer system 580, at least portions of the contents of the computer program product to the secondary storage 584, to the ROM 586, to the RAM 588, and/or to other non-volatile memory and volatile memory of the computer system 580. The processor 582 may process the executable instructions and/or data structures in part by directly accessing the computer program product, for example by reading from a CD-ROM disk inserted into a disk drive peripheral of the computer system 580. Alternatively, the processor 582 may process the executable instructions and/or data structures by remotely accessing the computer program product, for example by downloading the executable instructions and/or data structures from a remote server through the network connectivity devices 592. The computer program product may comprise instructions that promote the loading and/or copying of data, data structures, files, and/or executable instructions to the secondary storage 584, to the ROM 586, to the RAM 588, and/or to other non-volatile memory and volatile memory of the computer system 580.

In some contexts, the secondary storage 584, the ROM 586, and the RAM 588 may be referred to as a non-transitory computer readable medium or a computer readable storage media. A dynamic RAM embodiment of the RAM 588, likewise, may be referred to as a non-transitory computer readable medium in that while the dynamic RAM receives electrical power and is operated in accordance with its design, for example during a period of time during which the computer system 580 is turned on and operational, the dynamic RAM stores information that is written to it. Similarly, the processor 582 may comprise an internal RAM, an internal ROM, a cache memory, and/or other internal non-transitory storage blocks, sections, or components that may be referred to in some contexts as non-transitory computer readable media or computer readable storage media.

While a number of systems and methods have been described herein, specific embodiments can include, but are not limited to:

In a first embodiment, a method of determining the likelihood of a slip or fall comprises receiving, by a detection application stored in a non-transitory memory and executed on a processor, a plurality of sensor readings from a plurality of movement sensors, wherein the plurality of movement sensors are associated with different areas of a worker's body; comparing, by the detection application, the plurality of sensor readings with a plurality of movement patterns stored in a database; determining, by the detection application, that at least one of the movement patterns of the plurality of movement patterns matches the plurality of sensor readings; and generating, by the detection application, an indication that a slip or fall is likely based on the plurality of sensor readings.

A second embodiment can include the method of the first embodiment, further comprising: receiving contextual information from one or more sensors; identifying a context in which the plurality of sensor readings are occurring based on the contextual information; and selecting the plurality of movement patterns from the database based on a context.

A third embodiment can include the method of the first or second embodiment, wherein the contextual information is based on at least one of location information, biometric information, environmental information, or any combination thereof.

A fourth embodiment can include the method of the second or third embodiment, wherein the contextual information comprises a type of activity.

A fifth embodiment can include the method of any of the first to fourth embodiments, wherein the plurality of sensor readings comprise a plurality of accelerometer readings.

A sixth embodiment can include the method of the fifth embodiment, wherein the plurality of accelerometer readings provide movement information, orientation information, or a combination of movement information and orientation information.

A seventh embodiment can include the method of any of the first to sixth embodiments, further comprising: sending the indication to a safety device, wherein the safety device engages a lifeline in response to receiving the indication.

An eighth embodiment can include the method of any of the first to seventh embodiments, further comprising: sending an alert to a management component in response to the indication.

A ninth embodiment can include the method of any of the first to eighth embodiments, further comprising: receiving a second plurality of sensor readings from the plurality of movement sensors; receiving an indication that the second plurality of sensor readings comprise a slip or fall movement pattern; and updating the movement patterns stored in the database with the second plurality of sensor readings.

A tenth embodiment can include the method of the ninth embodiment, further comprising: identifying the slip or fall movement pattern; extracting a predicting movement pattern from the second plurality of sensor readings, wherein the predicting movement pattern comprises a series of movements leading up to the slip or fall movement pattern; and storing the predicting movement pattern in the database.

In an eleventh embodiment, a method of determining the risk of a slip or fall comprises: receiving, by a management application stored in a non-transitory memory and executed on a processor, specifications for a work event, wherein the specifications comprise location information, height information, and work requirements; identifying, by the management application, a first plurality of prior movement patterns associated with the specifications; receiving, by the management application, a plurality of sensor readings from a plurality of sensors associated with the location information; selecting a second plurality of prior movement patterns from the first plurality of movement patterns based on the plurality of sensor readings; and determining a slip or fall risk rating for the work event based on the second plurality of prior movement patterns.

A twelfth embodiment can include the method of the eleventh embodiment, further comprising: determining safety requirements based on the plurality of sensor readings and the slip or fall risk rating.

A thirteenth embodiment can include the method of the twelfth embodiment, further comprising: comparing the safety requirements to information for a plurality of workers, and selecting a worker from a plurality of workers based on the comparing.

In a fourteenth embodiment, a system for predicting a slip or fall comprises: a plurality of movement sensors, wherein the plurality of movement sensors are associated with different areas of a worker's body; a receiver in signal communication with the plurality of movement sensors, wherein the receiver comprises a memory and a processor, wherein the memory comprises a detection application that when executed on the processor, configures the processor to: receive a plurality of sensor readings from the plurality of movement sensors; compare the plurality of sensor readings with a plurality of stored movement patterns; determine that at least one of the movement patterns of the plurality of movement patterns matches the plurality of sensor readings; and generate a warning of a slip or fall based on the determination that the at least one of the movement patterns of the plurality of movement patterns matches the plurality of sensor readings.

A fifteenth embodiment can include the system of the fourteenth embodiment, further comprising: a chest strap, wherein at least one of the movement sensors is coupled to the chest strap, and wherein the chest strap is configured to be disposed about a torso of the worker.

A sixteenth embodiment can include the system of the fourteenth or fifteenth embodiment, wherein the plurality of movement sensors comprises at least two accelerometers.

A seventeenth embodiment can include the system of any of the fourteenth to sixteenth embodiments, further comprising: one or more additional sensors in signal communication with the receiver, wherein the one or more additional sensors are configured to detect at least one of location information, biometric information, environmental information, or any combination thereof An eighteenth embodiment can include the system of any of the fourteenth to sixteenth embodiments, further comprising: one or more additional sensors in signal communication with the receiver, wherein the one or more additional sensors are configured to detect a chemical composition in an atmosphere around the worker.

A nineteenth embodiment can include the system of any of the fourteenth to eighteenth embodiments, wherein the plurality of sensor readings comprise movement information, orientation information, or a combination of movement information and orientation information.

A twentieth embodiment can include the system of any of the fourteenth to nineteenth embodiments, wherein the plurality of movement sensors comprise at least a first movement sensor associated with the worker's hand or arm and at least a second movement sensor associated with the worker's foot or leg.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A method of determining a likelihood of a slip or a fall, the method comprising:
   receiving a plurality of sensor readings from a plurality of sensors;
   determining specifications for a work event, wherein the specifications comprise location information, height information, and work requirements;
   receiving contextual information from an additional sensor, wherein the contextual information comprises at least one of location information or environmental information;
   filtering a plurality of movement patterns stored in a database to select at least one movement pattern from among the plurality of movement patterns, based on the contextual information, wherein the plurality of movement patterns correlate with the at least one of the environmental information or the location information;
   determining a movement pattern based on the plurality of sensors readings;
   comparing the movement pattern associated with the plurality of sensor readings with the selected at least one movement pattern; and
   generating, based on a slip or fall risk rating for the work event exceeding a predetermined threshold, an indication that a slip or a fall is likely, in response to determining that the movement pattern associated with the plurality of sensor readings matches the selected at least one movement pattern.

2. The method of claim 1, wherein the contextual information further comprises at least one of: a type of activity and biometric information.

3. The method of claim 1, wherein the plurality of sensor readings comprise a plurality of accelerometer readings.

4. The method of claim 3, wherein the plurality of accelerometer readings provide movement information, orientation information, or a combination of the movement information and the orientation information.

5. The method of claim 1, further comprising:
   sending the indication to a safety device, wherein the safety device engages a lifeline in response to receiving the indication.

6. The method of claim 1, further comprising:
   sending an alert to a management component in response to the indication.

7. The method of claim 1, further comprising:
   receiving a second plurality of sensor readings from the plurality of sensors;
   receiving an indication that the second plurality of sensor readings comprise a slip or fall movement pattern; and
   updating the plurality of movement patterns stored in the database with the second plurality of sensor readings.

8. The method of claim 7, further comprising:
   identifying the slip or fall movement pattern;
   extracting a predicting movement pattern from the second plurality of sensor readings, wherein the predicting movement pattern comprises a series of movements leading up to the slip or fall movement pattern; and
   storing the predicting movement pattern in the database.

9. A method of determining a risk of a slip or a fall, the method comprising:
   accessing, by a management application stored in a non-transitory memory and executed on a processor:
      specifications for a work event, wherein the specifications comprise location information, height information, and work requirements;
      a plurality of sensor readings from a plurality of sensors; and
      contextual information from an additional sensor, wherein the contextual information comprises at least one of location information or environmental information, the method further comprising:
   filtering, a plurality of movement patterns stored in a database, to select at least one of a movement pattern from the plurality of movement patterns based on the contextual information, wherein the plurality of movement patterns correlate with the at least one of the environmental information or the location information;
   determining a movement pattern based on the plurality of sensor readings;
   comparing, by the management application, the movement pattern associated with the plurality of sensor readings with the selected one or more movement patterns; and
   determining, by the management application, that a slip or a fall is likely, based on a slip or fall risk rating for the work event based on the worker's movement pattern associated with the plurality of sensor readings matching at least one of the selected one or more movement patterns.

10. The method of claim 9, further comprising:
    determining safety requirements based on the plurality of sensor readings and the slip or fall risk rating; and
    comparing the safety requirements to information for a plurality of workers, and selecting a worker from the plurality of workers based on the comparing.

11. The method of claim 10, further comprising:
    developing a new pattern by combining data from the additional sensor with the sensor reading of plurality of sensors, wherein the new patterns are developed for new movements not encountered previously.

12. The method of claim 9, further comprising:
    generating, by the management application, based on the slip or fall risk rating for the work event exceeding a predetermined threshold, an indication that a slip or a fall is likely.

13. The method of claim 12, further comprising:
    sending the indication to a safety device, wherein the safety device is configured to engage a lifeline attached to the worker in response to receiving the indication.

14. A system for predicting a slip or a fall, the system comprising:
    a plurality of sensors; and
    a receiver in signal communication with the plurality of sensors, wherein the receiver comprises a memory and a processor, and wherein the memory comprises a detection application that, when executed on the processor, configures the processor to:

receive a plurality of sensor readings from the plurality of sensors;

access, from the memory, specifications for a work event, wherein the specifications comprise location information, height information, and work requirements;

receive contextual information from one or more additional sensors, wherein the contextual information comprises at least one of location information or environmental information;

filter a plurality of movement patterns stored in a database to select at least one of a movement pattern from the plurality of movement patterns based on the contextual information, wherein the plurality of movement patterns correlate with the at least one of the environmental information or the location information;

determine a movement pattern based on the plurality of sensors readings;

compare the plurality of sensor readings with the selected one or more movement patterns; and generate, based on the slip or fall risk rating for the work event exceeding a predetermined threshold, an indication that a slip or a fall is likely, in response to determining that the plurality of sensor readings matches with the selected at least one movement pattern;

determining a movement pattern based on the plurality of sensors readings;

comparing the movement pattern associated with the plurality of sensor readings with the selected at least one movement pattern; and generating, based on a slip or fall risk rating for the work event exceeding a predetermined threshold, an indication that a slip or a fall is likely, in response to determining that the movement pattern associated with the plurality of sensor readings matches the selected at least one movement pattern.

15. The system of claim 14, further comprising:
a chest strap, wherein at least one of the plurality of sensors is coupled to the chest strap, and wherein the chest strap is configured to be disposed about a torso of the worker.

16. The system of claim 14, wherein the plurality of sensors comprises at least two accelerometers.

17. The system of claim 14, wherein the one or more additional sensors are further configured to detect the contextual information, wherein the contextual information comprises a chemical composition in an atmosphere around the worker.

18. The system of claim 14, wherein the plurality of sensor readings comprise movement information, orientation information, or a combination of the movement information and the orientation information.

19. The system of claim 14, wherein the plurality of sensors comprise at least a first movement sensor associated with the worker's hand or arm and at least a second movement sensor associated with the worker's foot or leg.

20. The system of claim 14, wherein the plurality of sensor readings comprise a plurality of accelerometer readings, and wherein the plurality of accelerometer readings provide movement information, orientation information, or a combination of the movement information and the orientation information.

* * * * *